United States Patent
Shah

(10) Patent No.: US 6,541,033 B1
(45) Date of Patent: Apr. 1, 2003

(54) THERMOSENSITIVE BIODEGRADABLE HYDROGELS FOR SUSTAINED DELIVERY OF LEPTIN

(75) Inventor: Subodh Shah, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/107,603

(22) Filed: Jun. 30, 1998

(51) Int. Cl.$^7$ .................. A61K 9/10; A61K 47/34; A61P 3/04
(52) U.S. Cl. .................. 424/486; 424/426; 514/909; 514/944
(58) Field of Search .................. 424/486, 423, 424/426; 514/909, 944

(56) References Cited

U.S. PATENT DOCUMENTS

| | | | |
|---|---|---|---|
| 4,675,189 A | 6/1987 | Kent | 424/490 |
| 4,695,463 A | 9/1987 | Yang | 424/440 |
| 4,695,623 A | 9/1987 | Stabinsky | 530/351 |
| 4,703,008 A | 10/1987 | Lin | 435/240 |
| 4,810,643 A | 3/1989 | Souza | 435/68 |
| 4,897,471 A | 1/1990 | Stabinsky | 536/27 |
| 4,999,291 A | 3/1991 | Souza | 435/69.1 |
| 5,075,222 A | 12/1991 | Hannum | 435/69.1 |
| 5,372,808 A | 12/1994 | Blatt | 424/85.4 |
| 5,410,016 A * | 4/1995 | Hubbell et al. | |
| 5,441,868 A | 8/1995 | Lin | 435/69.4 |
| 5,521,283 A * | 5/1996 | DiMarchi et al. | |
| 5,541,293 A | 7/1996 | Stabinsky | 530/351 |
| 5,547,933 A | 8/1996 | Lin | 514/8 |
| 5,581,476 A | 12/1996 | Osslund | 364/496 |
| 5,582,823 A | 12/1996 | Souza | 424/85.2 |
| 5,618,698 A | 4/1997 | Lin | 435/69.4 |
| 5,621,080 A | 4/1997 | Lin | 530/350 |
| 5,702,717 A * | 12/1997 | Cha et al. | |
| 5,711,958 A * | 1/1998 | Cohn et al. | |

FOREIGN PATENT DOCUMENTS

| | | |
|---|---|---|
| WO | 02 78629 | 1/1990 |
| WO | WO 91/05795 | 5/1991 |
| WO | WO 92/17505 | 10/1992 |
| WO | WO 94/17185 | 8/1994 |
| WO | WO 95/17206 | 6/1995 |
| WO | WO 96/05309 | 2/1996 |
| WO | WO 96/40912 | 12/1996 |
| WO | WO 97/00128 | 1/1997 |
| WO | WO 97/01010 | 1/1997 |
| WO | WO 97/01331 | 1/1997 |
| WO | WO 97/06816 | 2/1997 |
| WO | WO 97/13479 | 4/1997 |

OTHER PUBLICATIONS

Jackanicz, T., et al., "Polylactiv Acid as a Biodegradable Carrier for Contraceptive Steroids", *Contraception*, vol. 8(3), pp. 227–234, (1973).

Pellymounter, M., et al., "Effects of the Obese Gene Product on Body Weight Regulation in ob/ob Mice", *Science*, vol. 269, pp. 540–543, (1995).

Halaas, J., et al., "Weight–Reducing Effects of the Plasma Protein by the Obese Gene", *Science*, vol. 269, pp. 543–546, (1995).

(List continued on next page.)

*Primary Examiner*—Edward J. Webman
(74) *Attorney, Agent, or Firm*—Craig A. Crandall; Ron K. Levy; Steve M. Odre

(57) ABSTRACT

The present invention relates generally to the development of pharmaceutical compositions which provide for sustained release of biologically active polypeptides. More specifically, the invention relates to the use of thermosensitive, biodegradable hydrogels, consisting of a block copolymer of poly(d,l- or l-lactic acid)(PLA) or poly (lactide-co-glycolide)(PLGA) and polyethylene glycol (PEG), for the sustained delivery of biologically active agents, such as leptin.

9 Claims, 8 Drawing Sheets

OTHER PUBLICATIONS

Campfield, L., et al., "Recombinant Mouse OB Protein: Evidence for a Peripheral Signal Linking Adiposity and Central Neural Networks", *Science*, vol. 269, pp. 546–549, (1995).

Hutchinson, F., et al., "Biodegradable Polymers for the Sustained Release of Peptides", *Biochemical Society Transactions*, vol. 13, pp. 520–523, (1985).

Ford, C., et al., "Fusion Tails for Recovery and Purification of Recombinant Proteins", *Protein Expression and Purification*, vol. 2, pp. 95–107, (1991).

Zhang, Y., et al., "Positional cloning of the mouse obese gene and its human hologue", *Nature*, vol. 372, pp. 425–432, (1994).

Zhang, Y., et al., "Positional cloning of the mouse obese gene and its human hologue", *Nature, Correction* vol. 374, pp. 479, (1995).

Martini, L., et al., "Micellisation and Gelation of Triblock Copolymer of Ethylene Oxide and $\in$–Caprolactone,$CI_nE_m$-$CL_n$ in Aqueous Solution", *Journal Chemical Society Faraday Trans.*, vol. 90(13), pp. 1961–1966, (1994).

\* cited by examiner

THERMOSENSITIVE BIODEGRADABLE HYDROGELS FOR SUSTAINED DELIVERY OF LEPTIN

FIELD OF THE INVENTION

The present invention relates to the use of thermosensitive, biodegradable hydrogels, consisting of a block copolymer of poly(d,1- or 1-lactic acid)(PLA) or poly(lactide-co-glycolide)(PLGA) and polyethylene glycol (PEG), for the sustained delivery of biologically active agents.

BACKGROUND OF THE INVENTION

Due to recent advances in genetic and cell engineering technologies, proteins known to exhibit various pharmacological actions in vivo are capable of production in large amounts for pharmaceutical applications. Such proteins include erythropoietin (EPO), granulocyte colony-stimulating factor (G-CSF), interferons (alpha, beta, gamma, consensus), tumor necrosis factor binding protein (TNFbp), interleukin-1 receptor antagonist (IL-1ra), brain-derived neurotrophic factor (BDNF), kerantinocyte growth factor (KGF), stem cell factor (SCF), megakaryocyte growth differentiation factor (MGDF), osteoprotegerin (OPG), glial cell line derived neurotrophic factor (GDNF) and obesity protein (OB protein). OB protein may also be referred to herein as leptin.

Leptin is active in vivo in both ob/ob mutant mice (mice obese due to a defect in the production of the OB gene product) as well as in normal, wild type the OB gene product) as well as in normal, wild type mice. The biological activity manifests itself in, among other things, weight loss. See generally, Barinaga, "Obese" Protein Slims Mice, *Science* 269: 475–476 (1995). See PCT International Publication Number WO 96/05309, "Modulators of Body Weight, Corresponding Nucleic Acids and Proteins, and Diagnostic and Therapeutic Uses Thereof," herein incorporated by reference in its entirety.

The other biological effects of OB protein are not well characterized. It is known, for instance, that in ob/ob mutant mice, administration of leptin results in a decrease in serum insulin levels, and serum glucose levels. It is also known that administration of leptin results in a decrease in body fat. This was observed in both ob/ob mutant mice, as well as non-obese normal mice. Pelleymounter et al., *Science* 269: 540–543 (1995); Halaas et al., *Science* 269: 543–546 (1995). See also, Campfield et al., *Science*269: 546–549 (1995) (Peripheral and central administration of microgram doses of leptin reduced food intake and body weight of ob/ob and diet-induced obese mice but not in db/db obese mice.) In none of these reports have toxicities been observed, even at the highest doses.

Preliminary leptin induced weight loss experiments in animal models predict the need for a high concentration leptin formulation with chronic administration to effectively treat human obesity. Dosages in the milligram protein per kilogram body weight range, such as 0.5 or 1.0 mg/kg/day or below, are desirable for injection of therapeutically effective amounts into larger mammals, such as humans. An increase in protein concentration is thus necessary to avoid injection of large volumes, which can be uncomfortable or possibly painful to the patient. unfortunately, native human leptin is known to be relatively insoluble in an aqueous solution at hysiological pH at concentrations of approximately 10 mg/mL and above, often resulting in adverse injection site reactions. Moreover, kidney anatomical abnormalities have been found to be associated with leptin administration in certain settings, e.g. PEG-leptin.

Because proteins such as leptin generally have short in vivo half-lives and negligible oral bioavailability, they are typically administered by frequent injection, thus posing a significant physical burden on the patient (injection site reactions are particular problematic with many leptin formulations) and associated administrative costs. As such, there is currently a great deal of interest in developing and evaluating sustained-release formulations. Effective sustained-release formulations can provide a means of controlling blood levels of the active ingredient, and also provide greater efficacy, safety, patient convenience and patient compliance. Unfortunately, the instability of most proteins (e.g. denaturation and loss of bioactivity upon exposure to heat, organic solvents, etc.) has greatly limited the development and evaluation of sustained-release formulations.

Biodegradable polymer matrices have thus been evaluated as sustained-release delivery systems. Attempts to develop sustained-release formulations have included the use of a variety of biodegradable and non-biodegradable polymer (e.g. poly(lactide-co-glycolide)) microparticles containing the active ingredient (see e.g., Wise et al., *Contraception*, 8:227–234 (1973); and Hutchinson et al., *Biochem. Soc. Trans.*, 13:520–523 (1985)), and a variety of techniques are known by which active agents, e.g. proteins, can be incorporated into polymeric microspheres (see e.g., U.S. Pat. No. 4,675,189 and references cited therein).

Utilization of the inherent biodegradability of these materials to control the release of the active agent and provide a more consistent sustained level of medication provides improvements in the sustained release of active agents. Unfortunately, some of the sustained release devices utilizing microparticles still suffer from such things as: active agent aggregation formation; high initial bursts of active agent with minimal release thereafter; and incomplete release of active agent.

Other drug-loaded polymeric devices have also been investigated for long term, therapeutic treatment of various diseases, again with much attention being directed to polymers derived from alpha hydroxycarboxylic acids, especially lactic acid in both its racemic and optically active form, and glycolic acid, and copolymers thereof. These polymers are commercially available and have been utilized in FDA-approved systems, e.g., the Lupron Depot™, which consists of injectable microcapsules which release leuprolide acetate for about 30 days for the treatment of prostate cancer.

Various problems identified with the use of such polymers include: inability of certain macromolecules to diffuse out through the matrix; deterioration and decomposition of the drug (e.g., denaturation caused by the use of organic solvents); irritation to the organism (e.g. side effects due to use of organic solvents); low biodegradability (such as that which occurs with polycondensation of a polymer with a multifunctional alcohol or multifunctional carboxylic acid, i.e., ointments); and slow rates of degradation.

The use of polymers which exhibit reverse thermal gelation have also been reported. For example, Okada et al., Japanese Patent Application 2-78629 (1990) describe biodegradable block copolymers synthesized by transesterification of poly(lactic acid) (PLA) or poly(lactic acid)/glycolic acid (PLA/GA) and poly(ethylene glycol) (PEG). PEGs with molecular weights ranging from 200 to 2000, and PLA/GA with molecular weights ranging from 400 to 5000 were utilized. The resultant product was miscible with water and formed a hydrogel. The Okada et al. reference fails to provide any demonstration of sustained delivery of drugs using the hydrogels.

Cha et al., U.S. Pat. No. 5,702,717 (Dec. 30, 1997) describe systems for parenteral delivery of a drug comprising an injectable biodegradable block copolymeric drug delivery liquid having reverse thermal gelation properties, i.e., ability to form semi-solid gel, emulsions or suspension at certain temperatures. Specifically, these thermosensitive gels exist as a mobile viscous liquid at low temperatures, but form a rigid semisolid gel at higher temperatures. Thus, it is possible to use these polymers to design a formulation which is liquid at room temperature or at lower temperature and below, but gels once injected, thus producing a depot of drug at the injection site. The systems described by Cha et al. utilize a hydrophobic A polymer block comprising a member selected from the group consisting of poly($\alpha$-hydroxy acids) and poly(ethylene carbonates) and a hydrophilic B polymer block comprising a PEG. The Cha et al. system requires that less than 50% by weight hydrophobic A polymer block be utilized and greater than 50% by weight hydrophilic B polymer block be utilized. Interestingly, however, it appears that several of the disclosed hydrogels might not be commercially useful in that the lower critical solution temperature (LCST) for many of the gels is greater than 37° C. Although Cha et al. propose use of their hydrogels for controlled release of drugs, no such demonstration is provided.

Martini et al., *J. Chem. Soc.*, 90(13): 1961–1966 (1994) describe low molecular weight ABA type triblock copolymers which utilize hydrophobic poly($\epsilon$-caprolactone)(PCL) and PEG. Unfortunately, in vitro degradation rates for these copolymers was very slow, thus calling into question their ability as sustained-release systems.

Stratton et al., PCT/US97/13479 (WO 98/02142) Jan. 22, 1998, describe pharmaceutical compositions comprising a polymeric matrix having thermal gelation properties, for the delivery of proteins. The class of block copolymers described are generically referred to as polyoxyethylene-polyoxypropylene condensates (also known as Pluronics). Unfortunately, systems utilizing Pluronics suffer from the fact that they are toxic to body organs and are nonbiodegradable. Moreover, only high molecular weight Pluronics at higher concentrations (25–40 wt. %) exhibit thermoreversible gelation.

It is thus the object of the present invention to provide thermosensitive, biodegradable hydrogels for the sustained delivery of drugs such as leptin. The hydrogels of the present invention utilize copolymer compositions which provide for instant gelation, and which possess the necessary rate of degradation to make use of the hydrogels commercially practical.

SUMMARY OF THE INVENTION

In one embodiment, the present invention provides pharmaceutical compositions comprising an effective amount of a biologically active agent incorporated into a polymeric matrix, said polymeric matrix comprising a block copolymer which is biodegradable, exhibits thermal gelation behavior, and is capable of providing for the sustained-release of the biologically active agent. Importantly, the leptin containing pharmaceutical compositions of the present invention result in no kidney anatomical abnormalities, improve the solubility properties of the leptin at physiological pH, increase the stability of the leptin protein, provide for improved efficacy, and result in no adverse injection site reactions associated with leptin precipitation at the injection site.

In another embodiment, the present invention provides a method for the parenteral administration of a biologically active agent in a biodegradable polymeric matrix to a warm blooded animal, wherein a gel depot is formed within the body of said animal and the biologically active agent is released from the depot at a controlled rate concomitant with biodegradation of the polymeric matrix.

DETAILED DESCRIPTION OF THE INVENTION

Figure 1:
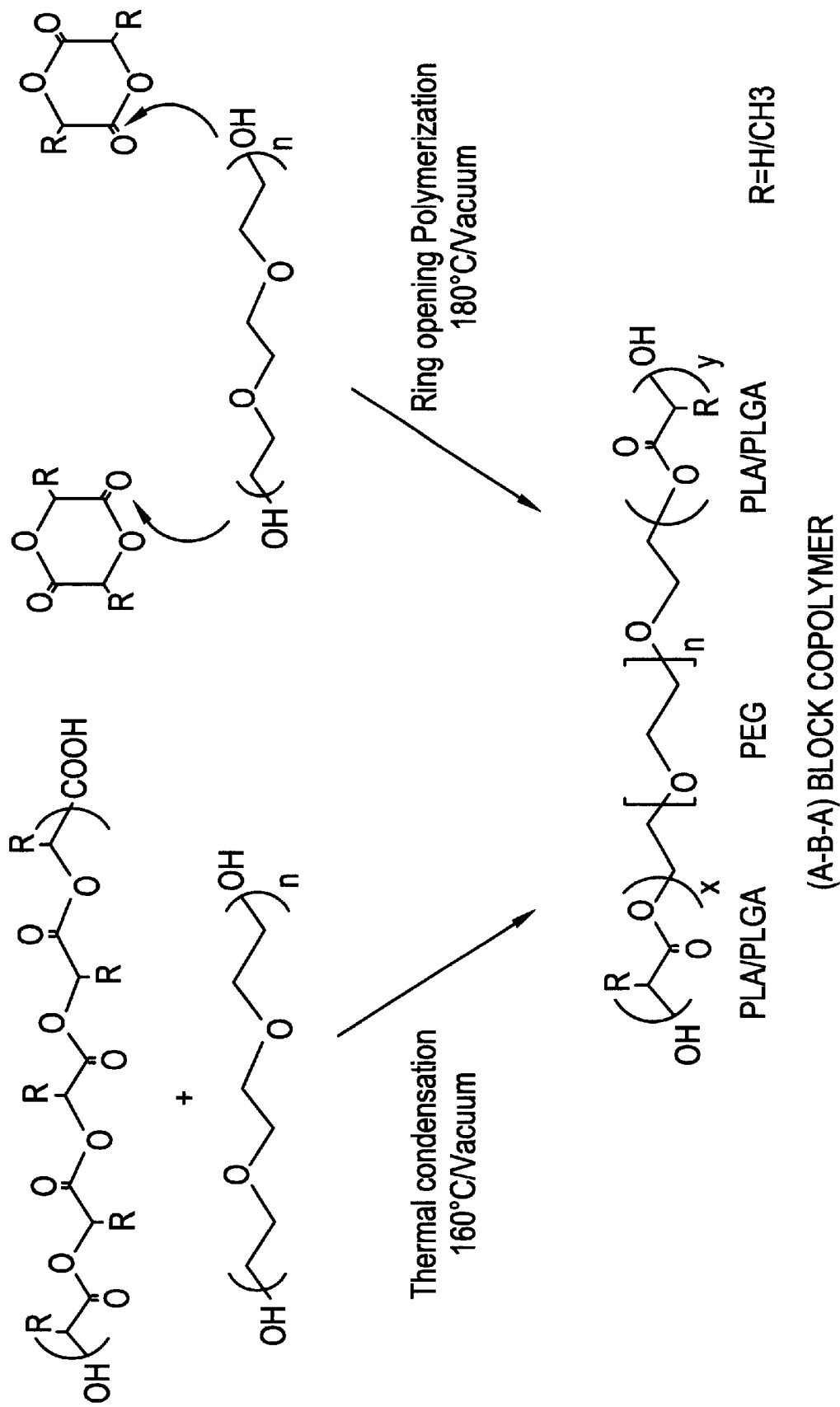
FIG. 1 depicts the two methods by which the A-B-A block copolymers of the present invention can be prepared.

As used herein, the following terms shall have the following meaning:

"Reverse thermal gelation" is defined as meaning the temperature below which a copolymer is soluble in water and above which the block copolymer forms a semi-solid, i.e. gels, emulsions, dispersions and suspensions.

"LCST", or lower critical solution temperature, is defined as meaning the temperature at which a biodegradable block copolymer undergoes reverse thermal gelation. For purposes of the present invention, the term "LSCT" can be used interchangeably with "reverse thermal gelation temperature". "Depot" is defined as meaning a drug delivery liquid which, following injection into a warm blooded animal, has formed a gel upon having the temperature raised to or above the LCST.

"Biodegradable" is defined as meaning that the block copolymer will erode or degrade in vivo to form smaller non-toxic components.

"Parenteral administration" is defined as meaning any route of administration other than the alimentary canal, including, for example, subcutaneous and intramuscular.

The present invention involves utilization of block copolymers having hydrophobic ("A") block segments and hydrophilic ("B") block segments. The block copolymers are triblock copolymers, e.g., ABA or BAB type block copolymers, which possess reverse thermal gelation properties and are biodegradable and biocompatible. Importantly, triblock copolymers of the present invention provide instant gelation and possess the necessary rate of degradation to be commercially useful.

Biodegradable hydrophobic A block segments contemplated for use include poly($\alpha$-hydroxy acid) members derived from or selected from the group consisting of homopolymers and copolymers of poly(lactide)s (d,l- or l-forms), poly(glycolide)s, polyanhydrides, polyorthoesters, polyetheresters, polycaprolactone, polyesteramides, polycarbonate, polycyanoacrylate, polyurethanes, polyacrylate, blends and copolymers thereof.

The term "PLGA" as used herein is intended to refer to a polymer of lactic acid alone, a polymer of glycolic acid alone, a mixture of such polymers, a copolymer of glycolic acid and lactic acid, a mixture of such copolymers, or a mixture of such polymers and copolymers. Preferably, the biodegradable A block polymer will be poly lactide-co-glycolide (PLGA), and the PLGA composition will be such that the necessary rate of gelation and rate of degradation are obtained.

The range of molecular weights contemplated for the polymers to be used in the present processes can be readily determined by a person skilled in the art based upon such factors the desired polymer degradation rate. Typically, the range of molecular weight for the A block will be 1000 to 20,000 Daltons.

Hydrophilic B block segments contemplated for use include polyethylene glycols having average molecular weights of between about 500 and 10,000.

The copolymer compositions for the block copolymers of the present invention are specially regulated to assure retention of the desired water-solubility and gelling properties, i.e., the ratios must be such that the block copolymers possess water solubility at temperatures below the LCST, and such that there is instant gelation under physiological conditions (i.e. pH 7.0 and 370C.) so as to minimize the initial burst of drug. In the hydrogels of the present invention the hydrophobic A block makes up 55% to 90%. by weight of the copolymer and the hydrophilic B block makes up 10% to 45% of the copolymer.

The concentration at which the block copolymers of the present invention remain soluble below the LCST are generally up to about 60% by weight, with 10%–30% preferred. The concentration utilized will depend upon the copolymer composition actually used, as well as whether or not a gel or emulsion is desired.

The thermosensitive block copolymers of the present invention can be prepared by thermal condensation. In a typical experiment, A-B-A block copolymers of PLGA/PLA (block A) and PEG (block B) are synthesized by mixing either homopolymer of poly lactide (PLA) or copolymer of poly lactide-co-gycolide (PLGA) with polyethylene glycol (PEG) and allowing di-hydroxy PEG to react with PLGA or PLA at 160° C. under reduced pressure. Different weight ratios of PLGA and PEG were used for thermal condensation to obtain a series of block copolymers with desirable copolymer composition and block lengths. Copolymer composition and relative block lengths were confirmed by $^1$H-NMR spectroscopy.

Alternatively, the copolymers could be synthesized in a melt process which involves ring opening polymerization of A block using B block as the initiator. In a typical experiment, the ABA triblock copolymer is prepared by stannous octoate catalyzed ring-opening polymerization of d,l-dilactide (or PLGA) using $\alpha,\omega$-dihydroxy-terminated PEG as the initiator. The mole ratio of B block to d,l-dilactide (or PLGA) is used to control the lengths of the A blocks, and provide a series of polymers with increasing A block contents and hydrophobicities. The relative A and B block lengths can be confirmed by $^1$H-NMR spectroscopy.

The process used to mix the copolymers with a biologically active agent and/or other materials involves dissolving the ABA block copolymers in an aqueous solution, followed by addition of the biologically active agent (in solution, suspension or powder), followed by thorough mixing to assure a homogeneous mixing of the biologically active agent throughout the copolymer. Alternatively, the process can involve the dissolving of the ABA block copolymer in a biologically active agent-containing solution. In either case, the process is conducted at a temperature lower than the gelation temperature of the copolymer and the material is implanted into the body as a solution which then gels or solidifies into a depot in the body. In the compositions of the present invention, the biologically active agent will generally have a concentration in the range of 0 to 200 mg/mL.

Buffers contemplated for use in the preparation of the biologically active agent-containing hydrogels are buffers which are all well known by those of ordinary skill in the art and include sodium acetate, Tris, sodium phosphate, MOPS, PIPES, MES and potassium phosphate, in the range of 25 mM to 500 mM and in the pH range of 4.0 to 8.5.

It is also envisioned that other excipients, e.g., various sugars, salts, or surfactants, may be included in the biologically active agent-containing hydrogels of the present invention in order to alter the LCST or rate of gelation of the gels. The ability to alter the rate of gelation and/or LCST is important and an otherwise non-useful hydrogel may be made useful by addition of such excipients. Examples of such sugars include glucose or sucrose in the range of 5% to 20%. Examples of such salts include sodium chloride or zinc chloride in the range of 0.5% to 10%.

As used herein, biologically active agents refers to recombinant or naturally occurring proteins, whether human or animal, useful for prophylactic, therapeutic or diagnostic application. The biologically active agent can be natural, synthetic, semi-synthetic or derivatives thereof. In addition, biologically active agents of the present invention can be perceptible. A wide range of biologically active agents are contemplated. These include but are not limited to hormones, cytokines, hematopoietic factors, growth factors, antiobesity factors, trophic factors, anti-inflammatory factors, small molecules and enzymes (see also U.S. Pat. No.

4,695,463 for additional examples of useful biologically active agents). One skilled in the art will readily be able to adapt a desired biologically active agent to the compositions of present invention.

Proteins contemplated for use would include but are not limited to interferon consensus (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582,823, and PCT Publication No. 94/17185, hereby incorporated by reference including drawings), stem cell factor (PCT Publication Nos. 91/05795, 92/17505 and 95/17206, hereby incorporated by reference including drawings), and leptin (OB protein) (see PCT publication Nos. 96/40912, 96/05309, 97/00128, 97/01010 and 97/06816 hereby incorporated by reference including figures).

The present leptin proteins used are preferably those with amino acid sequence of natural human leptin; see Zhang et al., *Nature* 372:425–432 (1994); see also, the Correction at *Nature* 374: 479 (1995), optionally with an N-terminal methionyl residue incident to bacterial expression is used. (See, Materials and Methods, infra). PCT publication No. WO 96/05309, published Feb. 22, 1996, entitled, "Modulators of Body Weight, Corresponding Nucleic Acids and Proteins, and Diagnostic and Therapeutic Uses Thereof" fully sets forth leptin protein and related compositions and methods, and is herein incorporated by reference. An amino acid sequence for human leptin protein is set forth at WO 96/05309 Seq. ID Nos. 4 and 6 (at pages 172 and 174 of that publication), and the first amino acid residue of the mature protein is at position 22 and is a valine residue. The mature protein is 146 residues (or 145 if the glutamine at position 49 is absent, Seq. ID No. 4). Specific leptin derivatives contemplated for use in the present invention include glycosylated leptins, Fc-leptin fusions, succinylated-leptin, and zinc derivatized leptin. It is desirable to have such leptin containing sustained-release compositions as such compositions could serve to enhance the effectiveness of either exogenously administered or endogenous leptin, or could be used, for example, to reduce or eliminate the need for exogenous leptin administration.

Moreover, because the materials utilized in the present invention are biocompatible and biodegradable, use of the leptin compositions of the present invention help prevent adverse injection site reactions normally associated with i.v. injections of leptin by improving the solubility properties of the leptin.

Also included are those polypeptides with amino acid substitutions which are "conservative" according to acidity, charge, hydrophobicity, polarity, size or any other characteristic known to those skilled in the art. See generally, Creighton, Proteins, W. H. Freeman and Company, N.Y., (1984) 498 pp. plus index, passim. One may make changes in selected amino acids so long as such changes preserve the overall folding or activity of the protein. Small amino terminal extensions, such as an amino-terminal methionine residue, a small linker peptide of up to about 20–25 residues, or a small extension that facilitates purification, such as a poly-histidine tract, an antigenic epitope or a binding domain, may also be present. See, in general, Ford et al., *Protein Expression and Purification* 2:95–107 (1991), which is herein incorporated by reference. Polypeptides or analogs thereof may also contain one or more amino acid analogs, such as peptidomimetics.

In general, comprehended by the invention are pharmaceutical compositions comprising effective amounts of chemically modified protein, or derivative products, together with pharmaceutically acceptable diluents, preservatives, solubilizers, emulsifiers, adjuvants and/or carriers needed for administration. (See PCT 97/01331 hereby incorporated by reference.) The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435–1712 (1990)).

The pharmaceutical compositions of the present invention are administered as a liquid via intramuscular or subcutaneous route and undergo a phase change wherein a gel is formed within the body, since the body temperature will be above the gelation temperature of the material. The release rates and duration for the particular biologically active agents will be a function of, inter alia, hydrogel density and the molecular weight of the agent.

Therapeutic uses of the compositions of the present invention depend on the biologically active agent used. One skilled in the art will readily be able to adapt a desired biologically active agent to the present invention for its intended therapeutic uses. Therapeutic uses for leptin are set forth in greater detail in the following publications (see PCT publication Nos. 96/40912, 96/05309, 97/00128, 97/01010 and 97/06816 hereby incorporated by reference including figures).

Therapeutic uses of leptin include weight modulation, the treatment or prevention of diabetes, blood lipid reduction (and treatment of related conditions), increasing lean body mass and increasing insulin sensitivity.

In addition, the present compositions may also be used for manufacture of one or more medicaments for treatment or amelioration of the conditions the biologically active agent is intended to treat.

In the sustained-release compositions of the present invention, an effective amount of active ingredient will be utilized. As used herein, sustained release refers to the gradual release of active ingredient from the polymer matrix, over an extended period of time. The sustained release can be continuous or discontinuous, linear or non-linear, and this can be accomplished using one or more polymer compositions, drug loadings, selection of excipients, or other modifications. The sustained release will result in biologically effective serum levels of the active agent (typically above endogenous levels) for a period of time longer than that observed with direct administration of the active agent. Typically, a sustained release of the active agent will be for a period of a week or more, preferably up to one month.

The following examples are offered to more fully illustrate the invention, but are not to be construed as limiting the scope thereof.

Materials

Low molecular weight (Mn 2000–6000) PLGA (poly Lactic acid-co-Glycolic acid) and PLA (poly Lactic acid) were synthesized by direct thermal condensation of glycolic acid and lactic acid at 180° C. under reduced pressure. High molecular weight PLGAs were obtained from B.I. Chemicals. Polyethylene glycols (PEG) were obtained from Fluka Chemicals. Leptin, zinc-leptin, GCSF, Fc-Leptin, and Fc-OPG were obtained from Amgen Inc. All other chemicals are from sources well known in the art.

Example 1

This example describes synthesis of a PLGA/PEG, A-B-A (PLGA-PEG-PLGA), block copolymer by thermal condensation. The thermal condensation method is generally depicted in FIG. 1.

30 g PLGA (75%/25% LA/GA ratio) (Mn 3740, MW 7050) and 10.7 g polyethylene glycol (MW 1000) were placed into a three-neck round bottom flask equipped with a thermometer, a nitrogen gas inlet, and a distillation condenser connected to a vacuum pump. After addition of the polymers, the temperature of the reaction mixture was raised slowly to 160° C. under nitrogen purging. The condensation reaction was further carried out at 160° C. for 14 hours under 500 millitorr pressure and with continuous bubbling of dry nitrogen gas. At the end of the condensation reaction, the reaction mixture was cooled, dissolved in methylene chloride and precipitated with an excess of cold isopropanol.

The isolated polymer was dried at 40° C. under vacuum for 48 hours. The molecular weight of the block copolymer was determined by gel permeation chromatography (GPC) using polystyrene standards. The copolymer composition and relative block lengths were determined by $^1$H-NMR.

The PLGA/PEG block copolymer dissolved either in 100 mM sodium acetate, pH 6.0, or 100 mM sodium phosphate, pH 7.0, exhibited a unique thermoreversible property (solution below room temperature and gel above room temperature, sol-gel-sol) with lower critical solution temperature (LCST) at about 30° C. to 35° C.

Example 2

This example describes the synthesis of PLGA/PEG, A-B-A (PLGA-PEG-PLGA), block copolymers using PLGA with different lactic acid to glycolic acid ratios.

The synthesis and characterization procedures described in Example 1 were utilized to prepare PLGA/PEG block copolymers using PLGA with different LA to GA ratios (see Table 1 below). The block copolymers listed below showed thermoreversibility (Sol-gel-sol) with LCST at about 30° C. to 35° C.

TABLE 1

| PLGA (LA/GA ratio) wt (g) | PEG 1000 wt (g) | PLGA/PEG wt ratio | PLGA/PEG calculated | Molar ratio by NMR |
|---|---|---|---|---|
| PLA (100%) 45 g (Mn 3480, MW 6590) | 17.55 g | 72/28 | 1.56 | 1.48 |
| PLGA (75/25%) 30 g (Mn 3740, MW 7090) | 11.74 g | 72/28 | 1.65 | 1.56 |
| PLGA (50/50%) 30 g (Mn 3480/MW 6590) | 10.71 g | 74/26 | 1.8 | 1.78 |
| PLGA (56/44%) 40 g (Mn 3480/MW 6590) | 15.60 g | 72/28 | 1.71 | 1.66 |

Example 3

This example describes the synthesis of PLGA/PEG, A-B-A (PLGA-PEG-PLGA), block copolymers using different weight ratios of PLGA and PEG.

The synthesis and characterization procedure described in Example 1 were utilized to prepare PLGA/PEG block copolymers with various PLGA to PEG ratios (see Table 2 below). All of the block copolymers listed below showed thermoreversibility (sol-gel-sol) with LCST in the range of 25° C.–35° C.

TABLE 2

| PLGA (75/25) Mn 3740, MW 7090 | PEG 1000 wt (g) | PLGA/PEG wt ratio | PLGA/PEG calculated | Molar ratio by NMR |
|---|---|---|---|---|
| 30 g | 9.47 g | 76/24 | 2.03 | |
| 40 g | 14.28 g | 74/26 | 1.79 | 1.70 |
| 40 g | 14.90 g | 73/27 | 1.72 | 1.65 |
| 30 g | 11.84 g | 72/28 | 1.65 | 1.56 |
| 30 g | 12.63 g | 70/30 | 1.53 | 1.50 |
| 30 g | 14.21 g | 68/32 | 1.36 | 1.32 |
| 30 g | 15.48 g | 66/34 | 1.24 | 1.17 |
| 30 g | 16.70 g | 64/36 | 1.15 | 1.08 |
| 30 g | 18.40 g | 62/38 | 1.05 | |

Example 4

This example describes the preparation of a leptin/hydrogel formulation and the methods used to determine the in vitro release kinetics, in vivo release kinetics, and pharmacokinetics of the leptin/hydrogel.

Preparation of leptin/hydrogel formulation

The PLGA/PEG block copolymer described in Example 1 was dissolved in 50 mM sodium acetate, pH 6.0. Leptin solution (formulated in 20 mM acetate, pH 4.8) was slowly added to the hydrogel solution and the mixture was gently swirled on an orbital shaker at 5° C. to assure a homogeneous mixing of leptin throughout the hydrogel solution. The final concentration of the copolymer in the final leptin/hydrogel formulation was 10–50% (w/w) and the leptin concentration was in the range of 0–100 mg/ml. The final leptin/hydrogel formulation was filtered through 0.2μfilter and stored either as a solution at 50° C. or stored as a frozen mass at −20° C.

Alternatively, the leptin/hydrogel formulation was prepared by dissolving the PLGA/PEG block copolymer in a leptin solution. The leptin solution concentration was varied to obtain desirable copolymer as well as the desired protein concentration in final formulation.

In vitro Release Study

Figure 2:
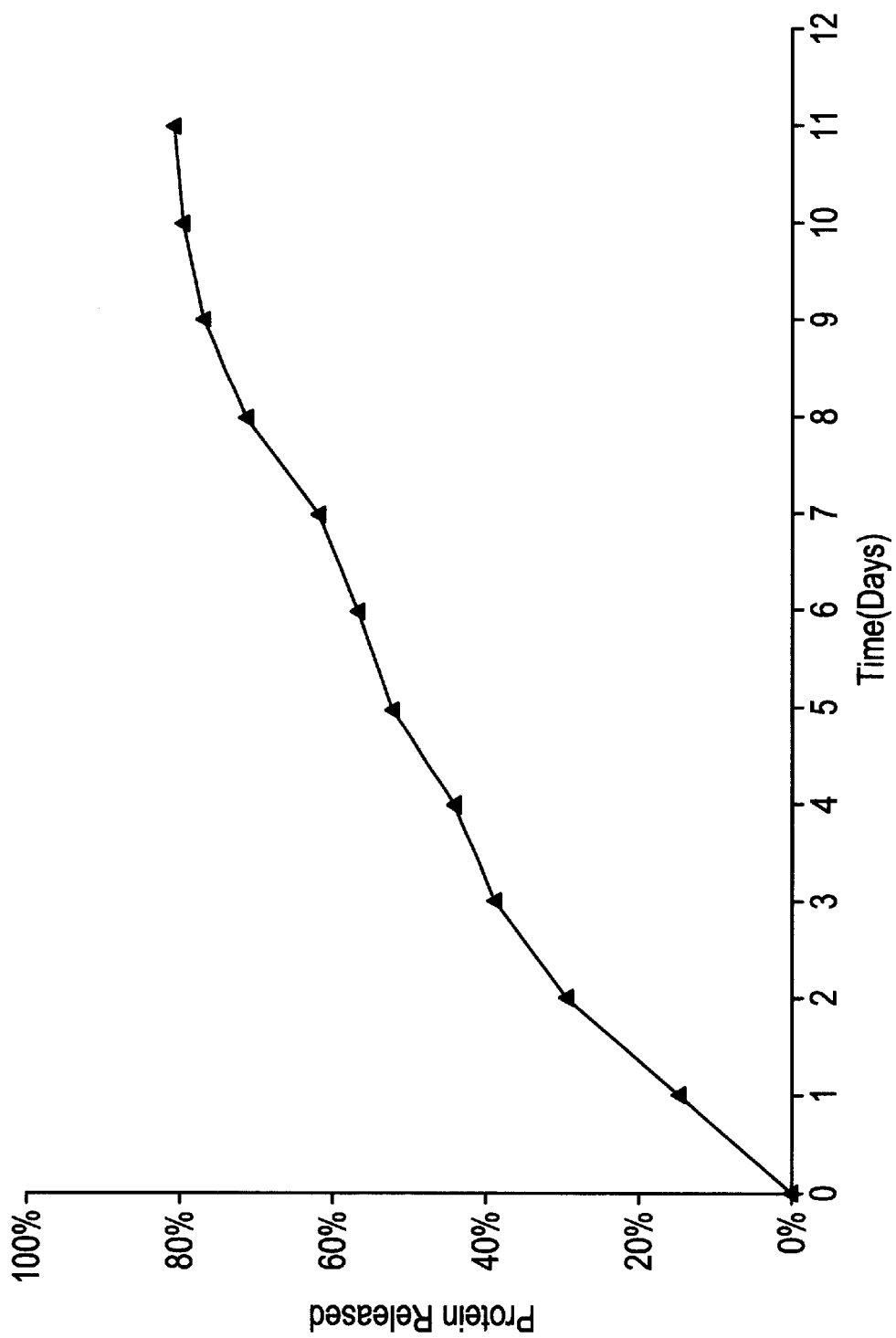
FIG. 2 depicts the in vitro release characteristics of leptin released from a hydrogel (PLGA/PEG (74%/26% w/w)). % protein released is plotted vs. time (days).
Figure 3:
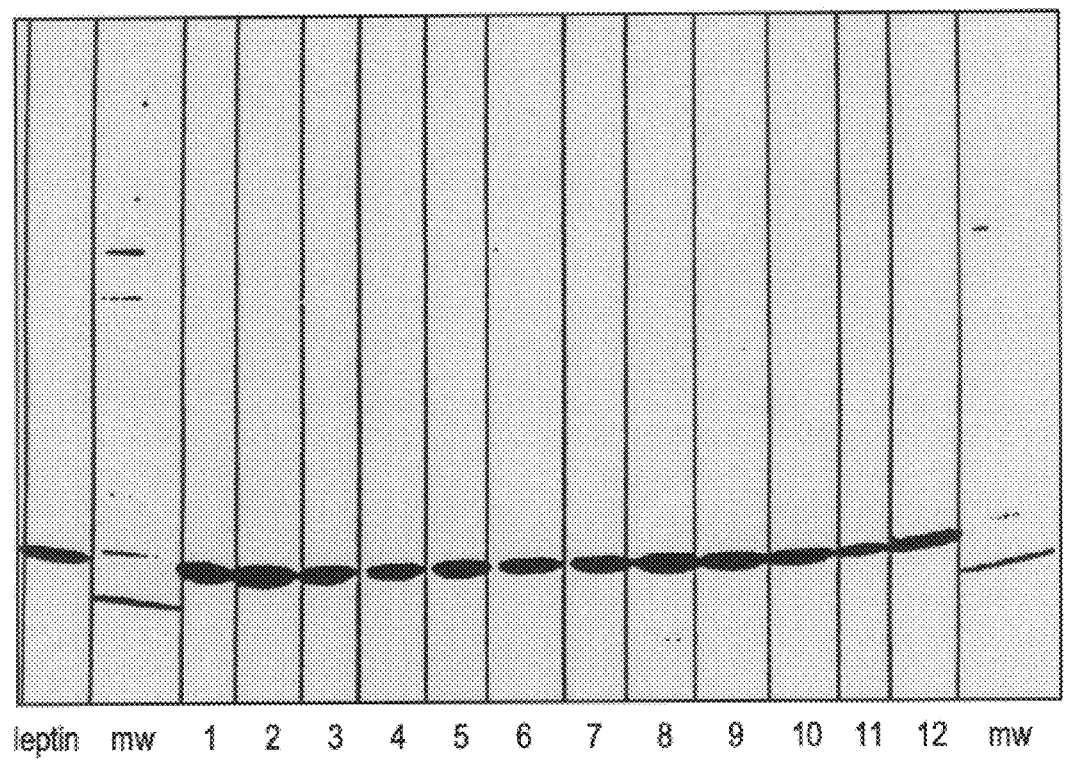
FIG. 3 is a photograph of an SDS-PAGE gel characterizing samples of leptin released from a hydrogel on various days. Lane 1 is a leptin standard; Lane 2 and 15 contain molecular weight markers; and Lanes 3–14 represent leptin samples at day 1–12, respectively.

The in vitro release of leptin from the leptin/hydrogel was carried out in 20 mM sodium phosphate, 5% sorbitol, pH 7.4, at 37° C. 1 ml of leptin/hydrogel solution formulation was placed in a glass vial at 37° C. Upon gelation of the leptin/hydrogel formulation, 1 ml of 20 mM phosphate, 5% sorbitol, pH 7.4, buffer was added directly above and in contact with the gel. The amount of leptin released in the top buffer phase was determined by UV spectrophotometer at 280 nm as well as by SEC-HPLC at 220 nm. To maintain a perfect sink condition the aqueous receptor phase above the gel was completely removed at definite time intervals and replaced by fresh buffer. The % leptin released over time is depicted in FIG. 2. The integrity of the leptin released from the hydrogel formulation was confirmed by HPLC (data not shown) and gel electrophoresis (SDS-PAGE) (see FIG. 3).

In vivo bioactivity

The in vivo bioactivity of leptin/hydrogel (74/26% (PLGA/PEG)(w/w)) formulations were evaluated in normal mice. Mice were injected subcutaneously (s.c.) with either: a) 0.1 ml of 20 mM acetate buffer, pH 4.8, (n=5, day 0 only); (b) 0.1 ml of 20 mg/ml leptin formulated in 20 mM acetate buffer, pH 4.8 (n=5, 100 mg/kg, day 0 only); (c) 0.1 ml of 2 mg/ml leptin formulated in 20 mM acetate buffer, pH 4.8 (n=5, 10 mg/kg, daily); (d) 0.1 ml of a leptin/hydrogel (74/26% (PLGA/PEG)(w/w)) formulation consisting of 20 mg/ml leptin, in 20 mM acetate, pH 4.8 (n=5, 100 mg/kg, day 0 only); (e) 0.2 ml of a leptin/hydrogel (74/26% (PLGA/PEG) (w/w)) formulation consisting of 20 mg/ml leptin, in 20 mM acetate, pH 4.8 (n=5, 200 mg/kg ,day 0 only); or (f) 0.1 ml of a hydrogel (74/26% (PLGA/PEG) (w/w)) control, formulated in 50 mM acetate, pH 6.0 (n=5, day 0 only).

Figure 4:
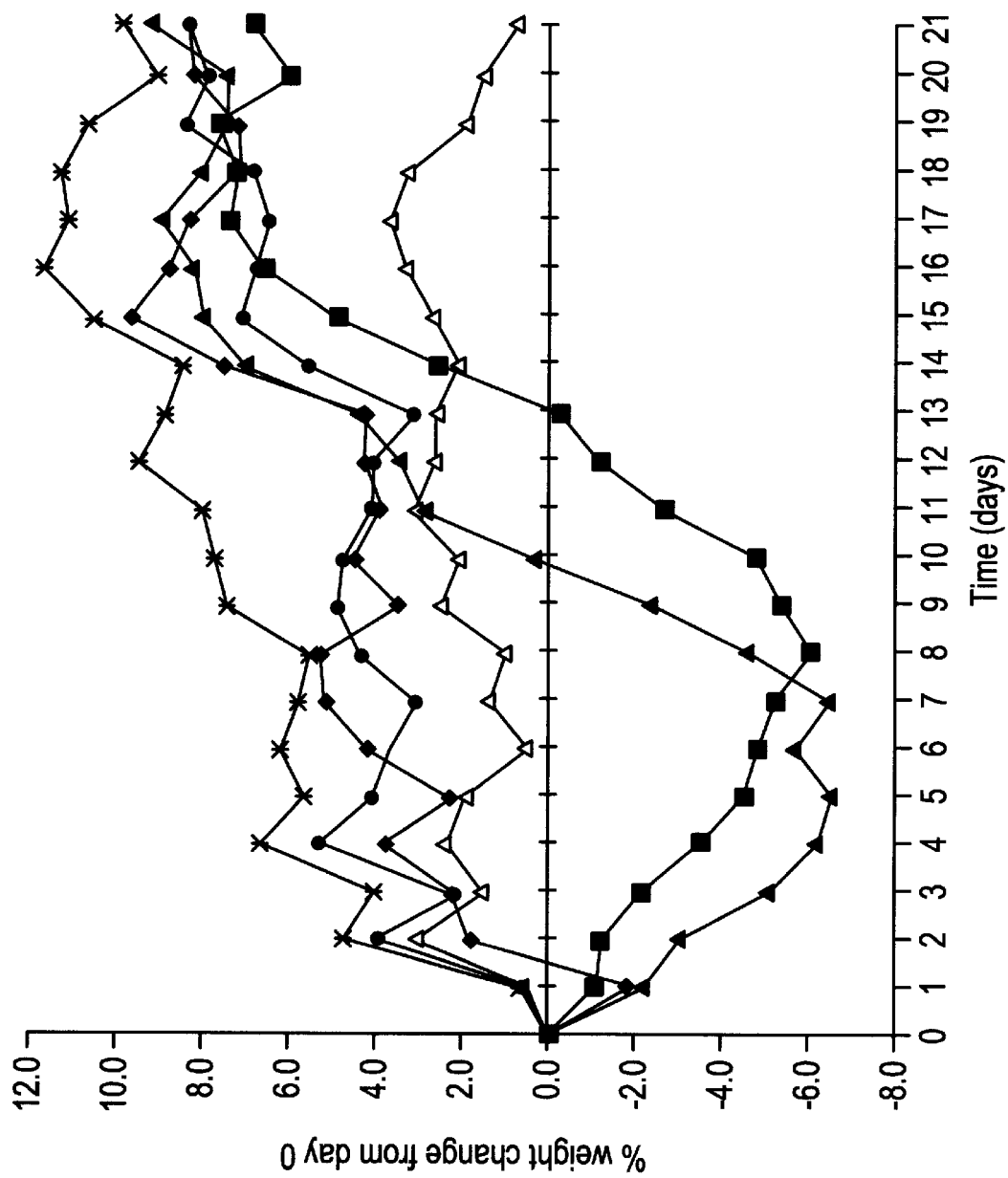
FIG. 4 depicts the in vivo bioactivity for various leptin-containing hydrogel (PLGA/PEG (74%/26% w/w)) formulations. The -*- depicts a 20 mM acetate, pH 4.8, buffer control, 100 $\mu$l on day 0; -•- depicts a hydrogel (74%/26%) control, 100 $\mu$on day 0; -♦- depicts leptin (20 mg/mL), 100 mg/kg, 100 $\mu$l on day 0; -Δ- depicts leptin (2 mg/mL), 10 mg/kg, 100 $\mu$l daily; -▼- depicts a leptin-containing hydrogel (PLGA/PEG (74%/26% w/w)), 20 mg/mL leptin, 100 mg/kg, 100 $\mu$l on day 0; and -■- depicts a leptin-containing hydrogel (PLGA/PEG (74%/26% w/w)), 20 mg/mL leptin, 200 mg/kg, 200 $\mu$l on day 0. % body weight change (from the day 0 body weight) is plotted vs. time (days).

% body weight change (from the day 0 body weight) was determined by weighing the animals daily until the body weight of the animals injected with sample (b), (d) and (e) reached the body weights of the animals injected with buffer control (sample (a)). Importantly, a single s.c. injection of 100 mg/kg leptin/hydrogel formulation (sample (d)) showed sustained weight loss in normal mice over a 10 day period. The duration of sustained weight loss effect was further extended up to 14 days when the dose was increased to 200 mg/kg (sample (e)). It was also observed that a single injection of 100 mg/kg or 200 mg/kg leptin/hydrogel at day '0' was more efficacious up to 14 days than daily injections of 10 mg/kg leptin without hydrogel. These results are depicted in FIG. 4.

Pharmacokinetics Study

Figure 5:
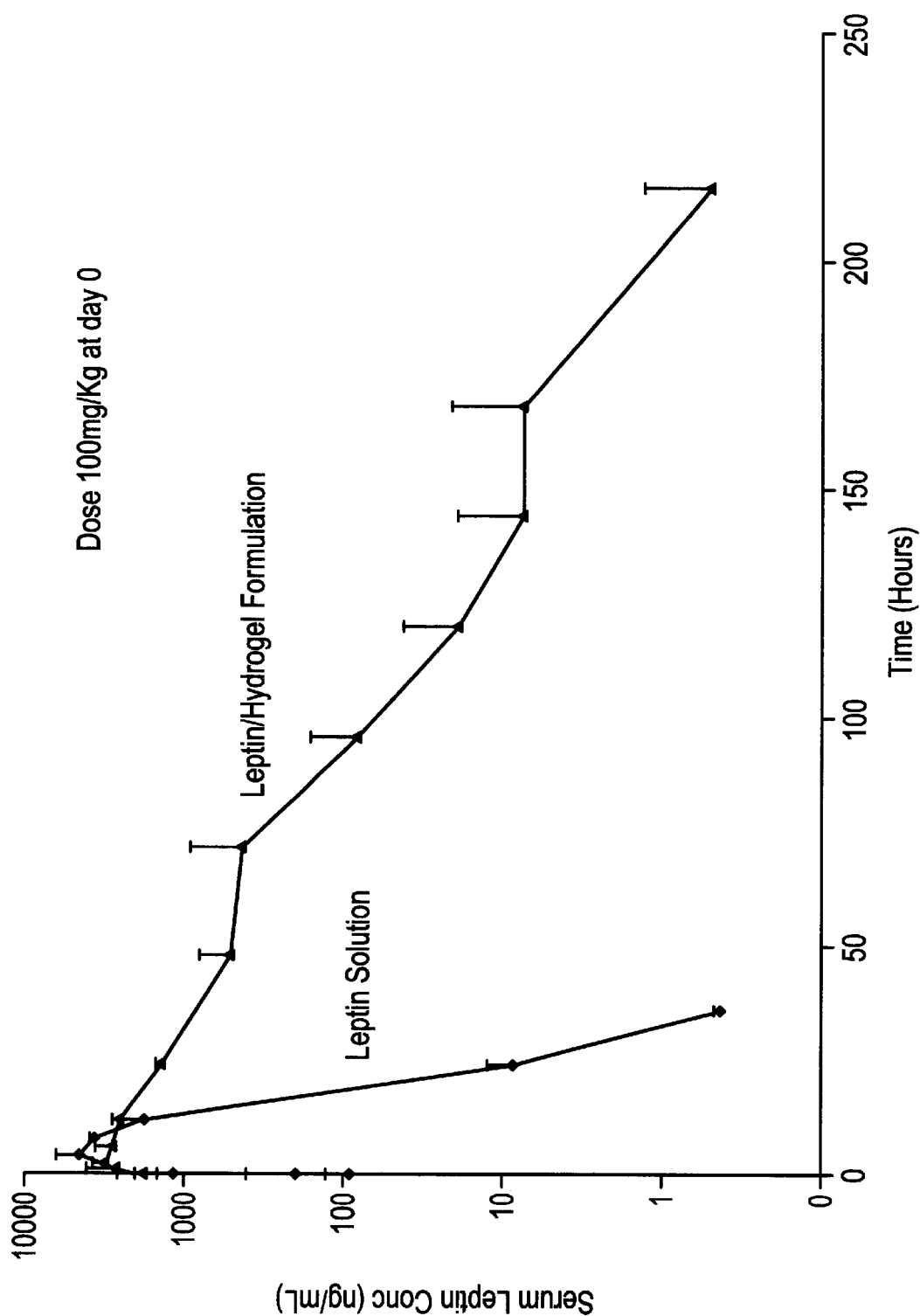
FIG. 5 depicts the pharmacokinetics for a leptin-containing hydrogel (PLGA/PEG (74%/26% w/w)) (-▼-) and leptin solution (-♦-). Serum leptin concentration (ng/mL) is plotted vs. time (hours).

A pharmacokinetics study was carried out in male rats. After a single s.c. injection of either: 1) 100 mg/kg dose of leptin (20 mg/ml) formulated in 20 mM acetate buffer, pH 4.8); or 2) a leptin/hydrogel (74/26% (PLGA/PEG)(w/w)) formulation consisting of 20 mg/ml leptin, in 20 mM acetate, pH 4.8, blood samples were collected at various time intervals and analyzed for leptin by ELISA assay. As shown in FIG. 5, serum concentrations of leptin were detectable for up to 168 hours for animals injected with the leptin/hydrogel formulation.

Example 5

This example describes the incorporation of G-CSF into the hydrogel and the results of in vitro release studies using the formulation.

Figure 6:
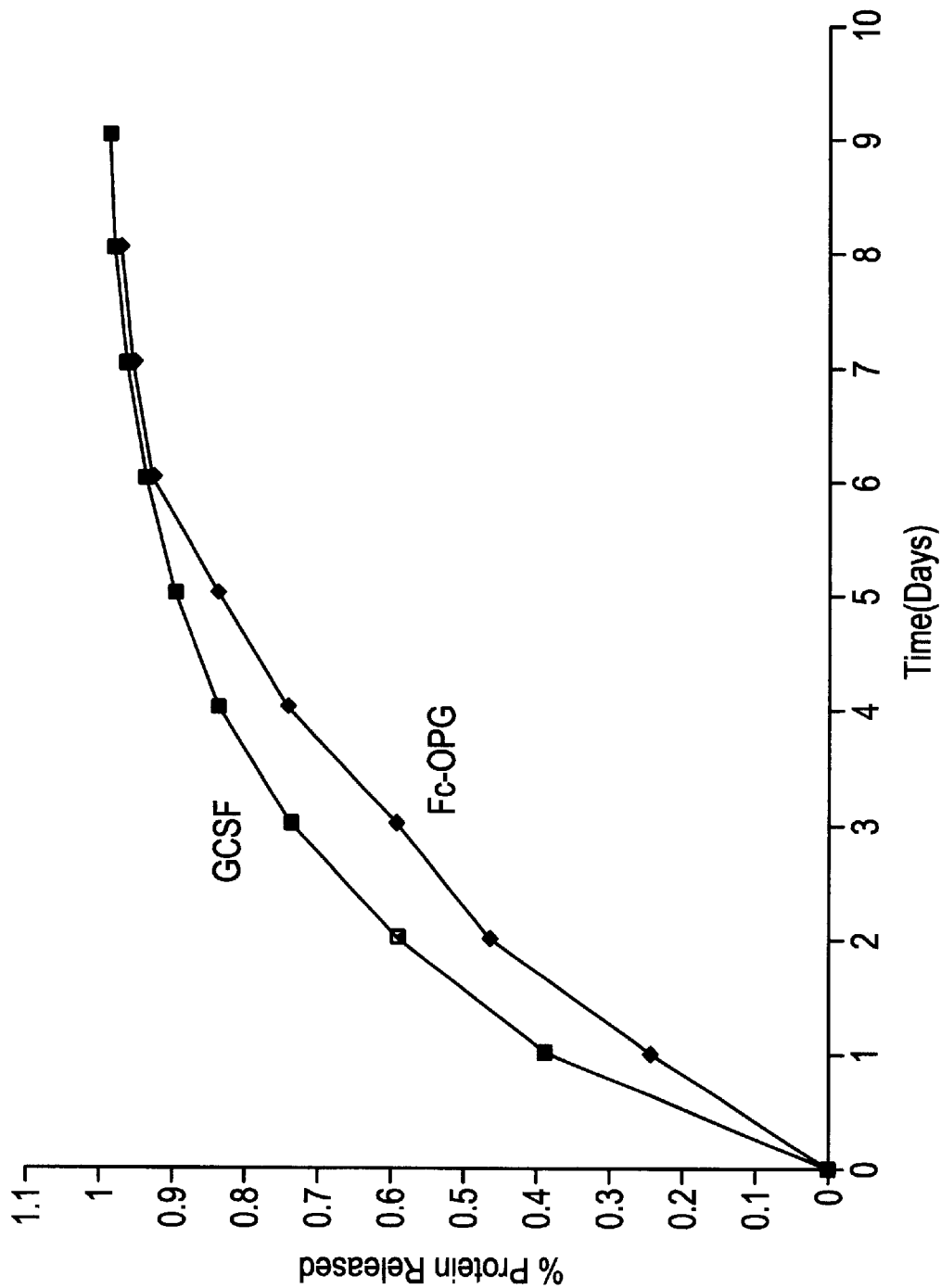
FIG. 6 depicts the in vitro release characteristics for GCSF from a GCSF-containing hydrogel (PLGA/PEG (74%/26% w/w)) (-♦-) and Fc-OPG from a Fc-OPG-containing hydrogel (PLGA/PEG (74%/26% w/w)) (-■-). % protein released is plotted vs. time (days).
Figure 7:
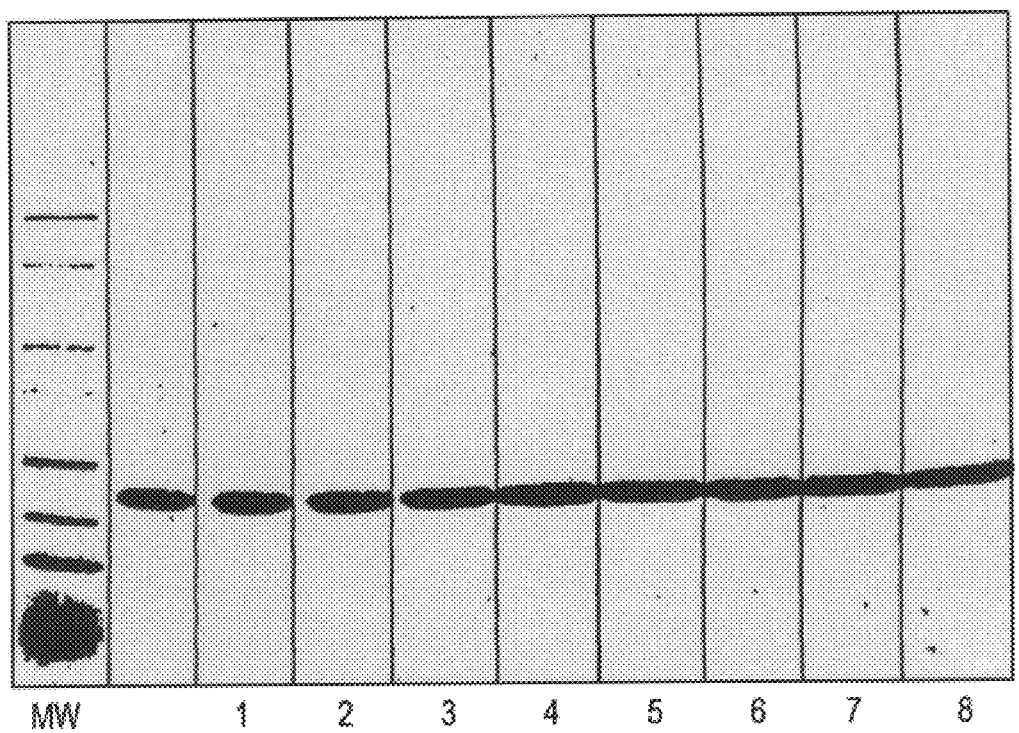
FIG. 7 is a photograph of an SDS-PAGE gel characterizing samples of leptin released from a hydrogel on various days. Lane 1 is a leptin standard; Lane 2 and 15 contain molecular weight markers; and Lanes 3–14 represent leptin samples at day 1–12, respectively.

GCSF solution (formulated in 10 mM acetate, 5% sucrose, pH 4.0) was added to the copolymer hydrogel solution (formulated in 20 mM acetate, pH 6.0) as described in Example 4. The final concentration of the copolymer in the GCSF/hydrogel formulation was 10–50% (w/w) and the GCSF concentration was in the range of 1–20 mg/ml. The in vitro release of GCSF from the hydrogel was carried out in 20 mM sodium phosphate buffer, pH 7.4, at 37° C. as described in Example 4. The % GCSF released over time is shown in FIG. 6. As depicted in FIG. 6, nearly 100% of the GCSF is released over a 9–10 day period of time. The integrity of the GCSF released from the hydrogel formulation was confirmed by HPLC (data not shown) and gel electrophoresis (SDS-PAGE) (see FIG. 7).

Example 6

This example describes the incorporation of an Fc-OPG protein into the hydrogel and the results of in vitro release studies using the Fc-OPG/hydrogel formulation.

The Fc-OPG/hydrogel formulation was prepared as described in Example 4 by adding Fc-OPG solution (formulated in 10 mM sodium acetate, 5% sorbitol, 0.02 mg/ml tween 20, pH 5.0) to the copolymer solution (formulated in 50 mM acetate, pH 6.0). The in vitro release of Fc-OPG from the hydrogel was carried out in 20 mM sodium phosphate buffer, pH 7.4, at 37° C. as described in Example 4. The % Fc-OPG released over time is shown in FIG. 6. As depicted in FIG. 6, nearly 100% of the Fc-OPG is released over a 8–9 day period of time.

Example 7

This example describes incorporation of the Zn:leptin suspension into PLGA/PEG hydrogel and the results of in vivo release kinetics of the leptin from the Zn:leptin/hydrogel.

Figure 8:
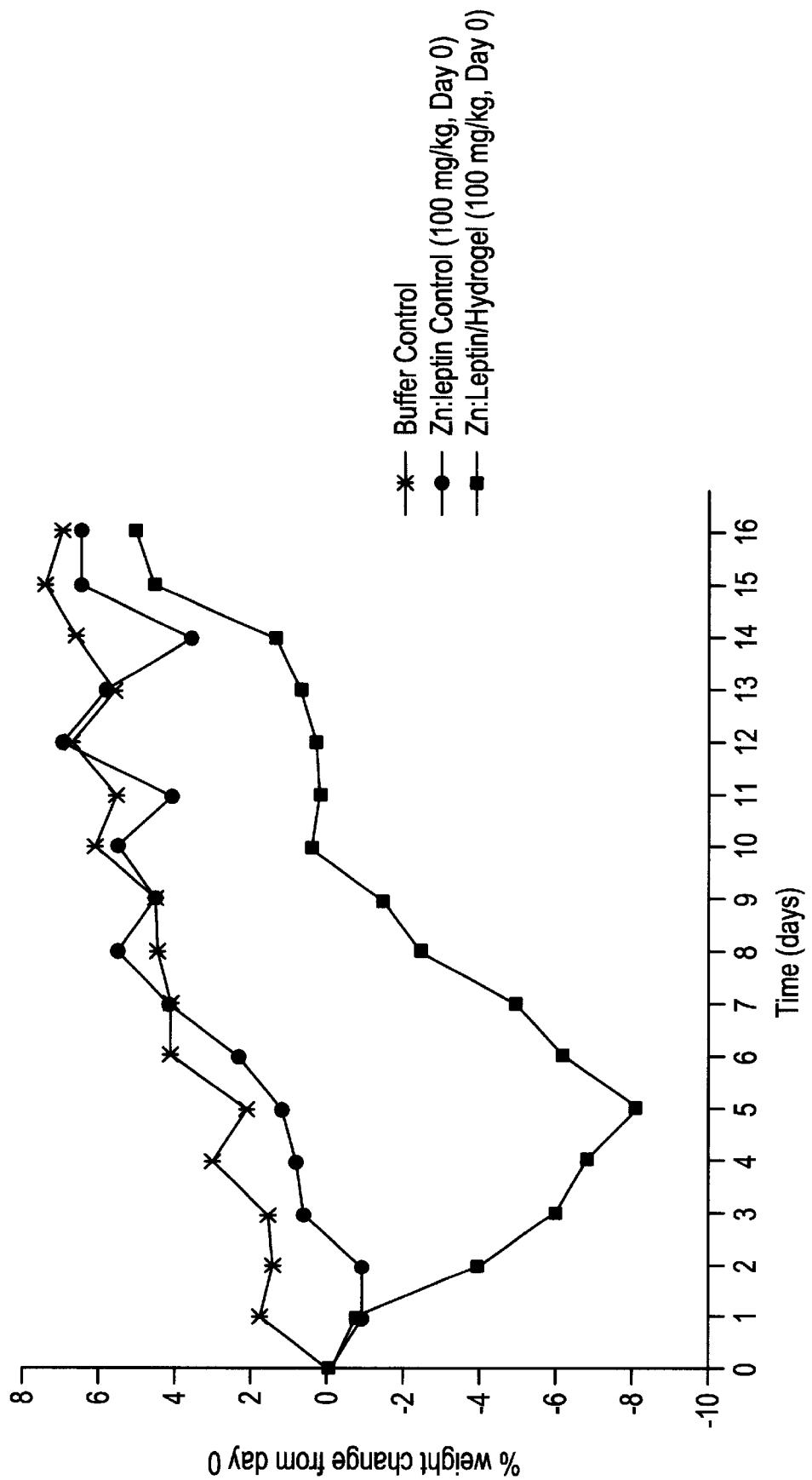
FIG. 8 depicts the in vivo bioactivity for a Zn:leptin-containing hydrogel (PLGA/PEG (74%/26% w/w)) formulation. -*- depicts a 20 mM acetate, pH 4.8, buffer control, 1001 $\mu$l on day 0; -•- depicts Zn:leptin, 100 mg/kg, 100 $\mu$l on day 0; and -■- depicts a Zn:leptin-containing hydrogel (PLGA/PEG (74%/26% w/w)), 20 mg/mL leptin, 100 mg/kg, 100 $\mu$l on day 0. % body weight change (from the day 0 body weight) is plotted vs. time (days).

The PLGA/PEG block polymers described in the examples above were hydrated in 100 mM Tris, pH 8.0 buffer. The final pH of the hydrogel solution was maintained between 6.5–7.0 and then a zinc chloride solution was added to the hydrogel to obtain a 0.1 mM $ZnCl_2$ concentration in the final hydrogel solution. To this hydrogel solution, a Zn:leptin suspension was added as described in Example 4. The final Zn:leptin concentration in the hydrogel described in this example was 20 mg/ml. The in vivo bioactivity of a Zn:leptin/hydrogel (74/26% (PLGA/PEG)(w/w)) formulation was carried out as described in Example 4. The results of the in vivo bioactivity studies are depicted in FIG. 8.

Example 8

This example describes the incorporation of Zn:GCSF into the PLGA/PEG hydrogel and the results of in vitro release studies using the formulation.

The PLGA/PEG block copolymer described in the examples above was hydrated in 100 mM PIPES, pH 7.5 buffer. The final pH of the hydrogel solution was maintained between 6.5–7.0 and then a zinc chloride solution was added to the hydrogel to obtain a 0.1 mM $ZnCl_2$ concentration in the final hydrogel solution. To this hydrogel solution, a Zn:GCSF suspension was added as described in Example 4. The in vitro release of GCSF from the hydrogel was carried out in 20 mM sodium phosphate buffer, pH 7.4, at 37° C., as described in Example 4. It was demonstrated that sustained release of GCSF could be obtained from these hydrogel formulations.

Example 9

This example describes the incorporation of GCSF-crystals in the PLGA/PEG hydrogel and the results of in vitro release studies using the formulation.

The block polymer described in the examples above was hydrated in 100 mM MES, pH 7.5 buffer. The final pH of the hydrogel solution was maintained between 6.5–7.0 and then a $MgCl_2$ solution was added to the hydrogel to obtain a 0.2M $MgCl_2$ concentration in the final hydrogel solution. To this hydrogel solution, a GCSF crystals suspension was added as described in Example 4. The in vitro release of GCSF from the hydrogel was carried out in 20 mM sodium phosphate buffer, pH 7.4, at 37° C., as described in Example 4. It was demonstrated that sustained release of GCSF could be obtained from these hydrogel formulations.

Example 10

This example describes the effect of various excipients on the LCST of PLGA/PLGA, A-B-A block copolymers. As indicated in Table 4 below, the addition of various sugars, salts, surfactants, etc. can effect the rate of gelation and LCST of the hydrogels.

TABLE 4

| Excipient Added | Effect on Gelation | Effect on LCST |
| --- | --- | --- |
| Sugars at 5%–20% (e.g. glucose, sucrose) | ↑ rate of gelation Firm gel | Lowered LCST |
| Salts at 0.5%–10% (e.g. $NaCl_2$, $ZnCl_2$, $Na_2SO_4$) | ↑ rate of gelation Firm gel | Lowered LCST |
| Surfactants (e.g. Tween, SDS) | ↓ rate of gelation Soft gel | ... |

TABLE 4-continued

| Excipient Added | Effect on Gelation | Effect on LCST |
|---|---|---|
| Glycerol at 2%–10% (e.g. NaCl$_2$, ZnCl$_2$, Na$_2$SO$_4$) | ↑ rate of gelation Firm gel | Lowered LCST |
| Polyethylene glycol at 5%–20% | ↓ rate of gelation Soft gel | Increased LCST |

The present invention has been described in terms of particular embodiments found or proposed to comprise preferred modes for the practice of the invention. It will be appreciated by those of ordinary skill in the art that, in light of the present disclosure, numerous modifications and changes can be made in the particular embodiments exemplified without departing from the intended scope of the invention.

What is claimed is:

1. A pharmaceutical composition for the sustained administration of an effective amount of leptin, or a derivative, analog, fusion, conjugate, or chemically modified form thereof, comprising an injectable biodegradable polymeric matrix into which said leptin has been incorporated, said polymeric matrix having reverse thermal gelation properties; wherein said injectable polymeric matrix is maintained at a temperature below the lower critical solution temperature of said polymeric matrix, and wherein said polymeric matrix is a biodegradable block copolymer comprising:

(a) 55% to 90% by weight of a hydrophobic A polymer block and;

(b) 10% to 45% by weight of a hydrophilic B polymer block comprising a polyethylene glycol having an average molecular weight of between 500–10,000.

2. The composition of claim 1, wherein said hydrophobic A polymer block is poly lactide-co-glycolide (PLGA) having an average molecular weight of between 1000–20,000.

3. The composition of claim 1, wherein said block copolymer is a triblock copolymer having a configuration selected from the group consisting of ABA or BAB block segments.

4. The composition of claim 3, wherein said hydrophobic A polymer block comprises 74% by weight of said block copolymer and said hydrophilic B polymer block comprises 26% by weight of said block copolymer.

5. The composition of claim 4, further comprising an excipient which will vary the lower critical solution temperature and increase the rate of gelation of said block copolymer.

6. The composition of claim 1 wherein said modified form of leptin is selected from the group consisting of Fc-leptin fusion, glycosylated leptin, succinylated-leptin, and zinc derivatized leptin.

7. The composition of claim 1 wherein said leptin has increased stability under physiological conditions.

8. The composition of claim 1 wherein said leptin has improved solubility under physiological conditions.

9. The composition of claim 1 wherein said leptin has improved efficacy under physiological conditions.

* * * * *

UNITED STATES PATENT AND TRADEMARK OFFICE
CERTIFICATE OF CORRECTION

PATENT NO. : 6,541,033 B1
DATED : April 1, 2003
INVENTOR(S) : Shah, S.

It is certified that error appears in the above-identified patent and that said Letters Patent is hereby corrected as shown below:

Column 1,
Line 49, change "Science269" to -- Science 269 --
Line 64, change "unfortunately" to -- Unfortunately --
Line 66, change "hysiological" to -- physiological --

Column 4,
Line 54, change "1001" to -- 100 --

Column 5,
Line 5, "Depot" should begin a new paragraph
Line 57, remove the period after "370C.)" to -- 37° C) --

Column 6,
Line 8, remove the period after "160°C." to -- 160° C --

Column 7,
Line 23, change "Nature372" to -- Nature 372 --
Line 24, change "Nature374" to -- Nature 374 --

Column 8,
Line 64, remove the period after "180° C." to -- 180° C --

Column 9,
Lines 15 & 16, remove the period after "160° C." to -- 160° C --
Line 21, remove the period after "40° C." to -- 40° C --
Line 32, remove the period after "30° C." to -- 30° C --
Line 41, remove the period after "30° C." to -- 30° C --

Column 10,
Line 2, remove the period after "25° C." to -- 25° C --
Line 29, remove the period after "5° C." to -- 5° C --
Line 35, remove the period after "50° C." to -- 5° C --
Line 45, remove the period after "37° C." to -- 37° C --

Column 11,
Line 64, remove the period after "37° C." to -- 37° C --

UNITED STATES PATENT AND TRADEMARK OFFICE
CERTIFICATE OF CORRECTION

PATENT NO. : 6,541,033 B1
DATED : April 1, 2003
INVENTOR(S) : Shah, S.

It is certified that error appears in the above-identified patent and that said Letters Patent is hereby corrected as shown below:

Column 12,
Line 32, remove the period after "37° C.," to -- 37° C, --
Line 48, remove the period after "37° C.," to -- 37° C, --

Column 13,
Line 22, after "comprising an" add the word -- aqueous, --

Column 14,
Line 5, change "poly lactide-co-glycolide (PLGA)" to -- a poly(a-hydroxy acid) --
Line 18, after "copolymer" add -- as compared to a block copolymer which does not contain said excipient. --
Line 24, after "conditions" add -- as compared leptin preparations which have been incorporated into said polymeric matrix. --
Line 26, after "conditions" add -- as compared leptin preparations which have been incorporated into said polymeric matrix. --
Line 28, after "conditions" add -- as compared leptin preparations which have been incorporated into said polymeric matrix. --

Signed and Sealed this

Fifth Day of August, 2003

JAMES E. ROGAN
*Director of the United States Patent and Trademark Office*